(12) United States Patent
    Eubanks

(10) Patent No.: US 10,125,080 B2
(45) Date of Patent: Nov. 13, 2018

(54) USE OF ACID ANHYDRIDE ACCELERANTS FOR THE PRODUCTION OF HIGH PURITY POLYOL ESTERS

(71) Applicant: CARGILL, INCORPORATED, Wayzata, MN (US)

(72) Inventor: John Eubanks, Ocean Springs, MS (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 15/741,658

(22) PCT Filed: Jul. 8, 2016

(86) PCT No.: PCT/US2016/041534
§ 371 (c)(1),
(2) Date: Jan. 3, 2018

(87) PCT Pub. No.: WO2017/008024
PCT Pub. Date: Jan. 12, 2017

(65) Prior Publication Data
US 2018/0194712 A1    Jul. 12, 2018

Related U.S. Application Data

(60) Provisional application No. 62/190,559, filed on Jul. 9, 2015.

(51) Int. Cl.
| C07C 67/00 | (2006.01) |
| C07C 67/08 | (2006.01) |
| C11C 3/02 | (2006.01) |
| C11C 1/08 | (2006.01) |
| C11C 3/10 | (2006.01) |

(52) U.S. Cl.
CPC ............... *C07C 67/08* (2013.01); *C11C 1/08* (2013.01); *C11C 3/02* (2013.01); *C11C 3/10* (2013.01)

(58) Field of Classification Search
CPC ...................................................... C07C 67/08
See application file for complete search history.

(56) References Cited

U.S. PATENT DOCUMENTS

| 2,766,273 | A | 10/1956 | Canapary et al. |
| 2,874,175 | A | 2/1959 | Ward et al. |
| RE28,729 | E | 3/1976 | Yetter |
| 4,319,049 | A | 3/1982 | Rogier |
| 6,939,980 | B2 | 9/2005 | Memita et al. |
| 8,399,697 | B2 | 3/2013 | Weber et al. |
| 8,524,937 | B2 * | 9/2013 | Adamzik ................ C07C 67/08 560/183 |
| 2012/0190883 | A1 | 7/2012 | Frey et al. |

OTHER PUBLICATIONS

Mattson, et al., "Esterification of hydroxy compounds by fatty acid anhydrides", The Journal of Lipid Research, 5, 1964, 374-377.

* cited by examiner

*Primary Examiner* — Yevgeny Valenrod
*Assistant Examiner* — Blaine G Doletski

(57) ABSTRACT

A method of producing high purity polyol esters comprises reacting a polyol with an excess amount of a linear or branched aliphatic monocarboxylic C3-20 acid to esterify less than the total amount of the polyol present to form an intermediate reaction composition having a hydroxyl value of from 7 to about 50 mg KOH/g. An anhydride of the corresponding linear or branched aliphatic monocarboxylic C3-20 acid is added to the intermediate reaction composition in an amount of from 1 to about 2.5 equivalents of available OH in the intermediate composition to form a reaction mixture. The reaction mixture is heated for 5-30 minutes or until all of the corresponding anhydride has reacted to form a reaction product. The reaction product is then de-acidified. No metal or acid catalyst or bleaching agents are present in any of the above reaction steps at a concentration above about 15 ppm.

20 Claims, 1 Drawing Sheet

USE OF ACID ANHYDRIDE ACCELERANTS FOR THE PRODUCTION OF HIGH PURITY POLYOL ESTERS

CROSS-REFERENCE TO RELATED APPLICATIONS

This application is a national phase application of international application PCT/US2016/041534, filed Jul. 8, 2016, and entitled USE OF ACID ANHYDRIDE ACCELERANTS FOR THE PRODUCTION OF HIGH PURITY POLYOL ESTERS, which application claims the benefit of U.S. Provisional Patent Application Ser. No. 62/190,559, filed on Jul. 9, 2015, entitled USE OF ACID ANHYDRIDE ACCELERANTS FOR THE PRODUCTION OF HIGH PURITY POLYOL ESTERS, both of which applications are hereby incorporated by reference herein in their entirety.

FIELD OF THE INVENTION

The present invention relates to preparation of polyol esters. More specifically, the present invention relates to production of high purity polyol esters.

BACKGROUND OF THE INVENTION

Esters of polyhydric alcohols, also known as polyol esters, are known in the industry for a number of uses, including for use as lubricants or plasticizers.

Polyol esters have been made by a number of manufacturing methods, such as by reacting polyols with linear or branched aliphatic monocarboxylic C3-20 acids in the presence of a Lewis acid comprising at least one element from groups 4 to 14 of the periodic table of the elements as catalyst, and optionally in the presence of an adsorbent, and steam treatment in the course of workup of the crude esters. See, e.g., US Patent Application Publication No. 2012/0190883 to Frey.

A method for manufacturing polyol esters is described in U.S. Pat. No. 8,399,697 to Weber, wherein polyols are reacted with linear or branched aliphatic monocarboxylic C3-20 acids in the presence of an adsorbent and steam treatment in the course of workup of the crude esters. Another method is described in U.S. Pat. No. 8,524,937 to Adamzik, wherein polyols are reacted with linear or branched aliphatic monocarboxylic C3-20 acids in the presence of catalysts and adsorbent by partial recycling of the aliphatic monocarboxylic acid removed into the esterification reaction or into subsequent esterification batches.

SUMMARY OF THE INVENTION

In certain applications, polyol esters are useful only when they are provided in a highly pure form, meaning that they contain very low amounts of acid or metal residues. This is particularly the case when the polyol esters are used in lubricants, for example, in refrigeration equipment. The presence of contaminants can lead to corrosion of equipment or degradation of materials. Conventional processes for producing high purity polyol esters may require excessively long reactions times that add to cost of production, and additionally may lead to degradation of the reactants or final products due to exposure to heat over a long period of time.

It has been found that high purity polyol esters may be efficiently prepared by conducting a reaction of a polyol with an excess amount of a linear or branched aliphatic monocarboxylic C3-20 acid to esterify less than the total amount of the polyol present, followed by reaction of an anhydride of the corresponding linear or branched aliphatic monocarboxylic C3-20 acid to form a reaction product.

More specifically, a method of producing high purity polyol esters comprises:

a) reacting a polyol with an excess amount of a linear or branched aliphatic monocarboxylic C3-20 acid to esterify less than the total amount of the polyol present to form an intermediate reaction composition having a hydroxyl value of from 7 to about 50 mg KOH/g;

b) adding an anhydride of the corresponding linear or branched aliphatic monocarboxylic C3-20 acid to the intermediate reaction composition in an amount of from 1 to about 2.5 equivalents of available OH in the intermediate composition to form a reaction mixture;

c) heating the reaction mixture for 5-30 minutes or until all of the corresponding anhydride has reacted to form a reaction product; and d) de-acidifying the reaction product;

wherein no catalyst comprising metal, halogen or sulfur or bleaching agent comprising metal, halogen or sulfur is present in any of the above method steps a-c at a concentration above about 15 ppm.

Because the initial reaction is only run long enough to form an intermediate reaction composition having a hydroxyl value of from 7 to about 50 mg KOH/g, the reaction may be carried out for a much shorter duration and/or under less aggressive reaction conditions than a conventional esterification reaction. The reaction is then completed in efficient manner by adding an anhydride of the corresponding linear or branched aliphatic monocarboxylic C3-20 acid.

Because the process of the present invention does not require excessively long reactions time to achieve complete esterification, the cost of production of high purity polyol esters is reduced. The polyol esters produced in embodiments of the present process are transparent, light colored and of high quality. Also, polyol esters produced by the process of invention have excellent thermal, oxidative and hydrolytic stability. Additionally, because the process is carried out so that no catalyst comprising metal, halogen or sulfur or bleaching agent comprising metal, halogen or sulfur is present in any of the above method steps a-c at a concentration above about 15 ppm, the resulting polyol esters have high purity.

BRIEF DESCRIPTION OF THE DRAWINGS

The accompanying drawings, which are incorporated in and constitute a part of this application, illustrate several aspects of the invention and together with a description of the embodiments serve to explain the principles of the invention. A brief description of the drawings is as follows.

DETAILED DESCRIPTION OF PRESENTLY PREFERRED EMBODIMENTS

Figure 1:
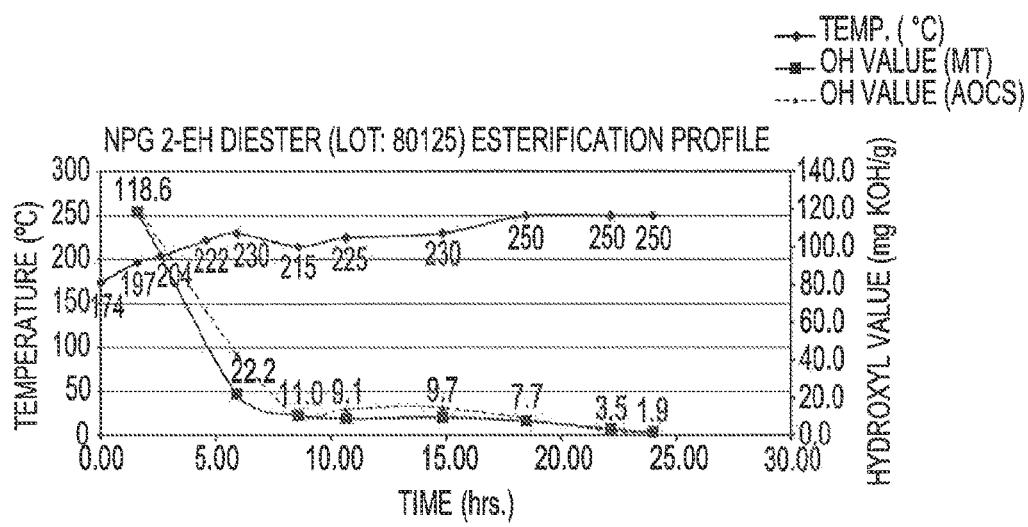
FIG. 1 is a graph showing the reaction time vs reaction temperature of an embodiment of the present method of preparation. "NPG" refers to neopentyl glycol.

The embodiments of the present invention described below are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

As noted above, conducting a stepwise reaction where a polyol is reacted with a linear or branched aliphatic monocarboxylic C3-20 acid to a limited amount, i.e. only to esterify less than the total amount of the polyol present to form an intermediate reaction composition having a hydroxyl value of from 7 to about 50 mg KOH/g, provides significant advantage in not exposing the reactants to prolonged reaction conditions. In an embodiment, the intermediate reaction composition has a hydroxyl value of from about 8 to about 40 mg KOH/g. In an embodiment, the intermediate reaction composition has a hydroxyl value of from about 9 to about 30 mg KOH/g. In another embodiment, the intermediate reaction composition has a hydroxyl value of from about 10 to about 25 mg KOH/g.

Advantageously, in an embodiment one or more of the reaction steps a-c described above are carried out at ambient pressure. For purposes of the present invention, "ambient pressure" means that the reactants during the relevant reaction step are not subjected to vacuum or enhanced pressure. In an embodiment, one or more of the reaction steps a-c described above are carried out in a vacuum, wherein the pressure of the reaction vessel is no less than about 0.7 atmospheres, or a pressure of no less than about 0.8 atmospheres. In an embodiment, one or more of the reaction steps a-c described above are carried out under pressure, wherein the pressure of the reaction vessel is no more than about 1.3 atmospheres, or a pressure of no more than about 1.2 atmospheres.

In an embodiment, step a) as described above is carried out at a temperature of from about 150° C. to about 230° C. In an embodiment, step a) as described above is carried out at a temperature of from about 170° C. to about 230° C. In embodiments wherein aliphatic monocarboxylic C3-20 acid is linear, step a) in particular advantageously carried out at a temperature of from about 150° C. to about 200° C. In an embodiment, step a) as described above is carried out for at time of about 3 to about 5 hours. In an embodiment, step a) as described above is carried out in the absence of oxygen. In an embodiment, step a) as described above is carried out in an inert gas atmosphere. In an embodiment, step a) is carried out under a blanket of an inert gas. In an embodiment, step a) is carried out with sparging of an inert gas. In an embodiment, the inert gas is nitrogen. In an embodiment, the inert gas is argon.

In an embodiment, step c) as described above is carried out a temperature of from about 40° C. to about 170° C. In an embodiment, step c) is carried out at a temperature that is no more than about 30° C. less than the boiling point at the pressure of the reaction vessel of the linear or branched aliphatic monocarboxylic C3-20 acid. In an embodiment, step c) is carried out at a temperature that is no more than about 20° C. less, or about 10° C. less than the boiling point at the pressure of the reaction vessel of the linear or branched aliphatic monocarboxylic C3-20 acid.

In an embodiment, one or more of steps a-c as described above are carried out in the presence of an adsorbent. In an embodiment, the adsorbent is activated carbon.

As noted above, no catalyst comprising metal, halogen or sulfur or bleaching agent comprising metal, halogen or sulfur is present in any of the above method steps a-c above a concentration of less than or equal to about 15 ppm. In an embodiment, no catalyst comprising metal, halogen or sulfur or bleaching agent comprising metal, halogen or sulfur is present in any of the above method steps a-c above a concentration of less than or equal to about 10 ppm, or above 7 ppm, or above 5 ppm or above 3 ppm, or about 1 ppm. It has been found that minimizing the amount of catalyst comprising metal, halogen or sulfur or bleaching agent comprising metal, halogen or sulfur during the reaction phases of the present method is beneficial, because this facilitates avoidance of the presence of such undesirable materials in the final product. While not being bound by theory, it is believed that having such materials present during the reaction steps (i.e. during any of the above method steps a-c) cause these materials to be extremely difficult to remove. Surprisingly, when such materials are added after completion of the reaction steps to facilitate purification or separation steps, the materials are not as difficult to separate from the final product.

In an embodiment, no catalyst comprising metal, halogen or sulfur or bleaching agent comprising metal, halogen or sulfur is present in the final product above a concentration of about 1 ppm. In an embodiment, no catalyst comprising metal, halogen or sulfur or bleaching agent comprising metal, halogen or sulfur is present in the final product above a concentration of about 0.5 ppm. It has been found that when the amount of catalyst comprising metal, halogen or sulfur or bleaching agent comprising metal, halogen or sulfur present in the reaction steps is limited as described above, the undesired materials can be removed by conventional product work-up techniques, such as water removal distillation, without resorting to extraordinary or expensive purification steps.

The reaction product formed by steps a-c is then de-acidified in an appropriate way. In an embodiment, the reaction product is de-acidified by heating and applying vacuum at levels effective to remove acid. In an embodiment, when the acid has a boiling point higher than 228° C., a vacuum of from about 30 to about 50 mmHg is applied to minimize degradation of the desired polyol ester final product. In an embodiment, the reaction product is heated to a temperature no higher than about 230° C.

In an embodiment, the de-acidifying step d) comprises steam stripping by injection of steam into the reaction product and/or by addition of water to the reaction product with co-distillation of water and undesired components in the reaction product. In a preferred embodiment, the de-acidifying step d) comprises addition of water to the reaction product with co-distillation of water and undesired components.

In another embodiment, the de-acidifying step d) comprises addition of a solid alkaline substance, for example basic silicon dioxide, basic aluminum oxide or sodium carbonate, sodium hydrogen carbonate, calcium carbonate, or sodium hydroxide in solid form, with subsequent removal of byproducts. In another embodiment, the de-acidifying step d) comprises addition of a lime or a dilute caustic wash at temperatures below about 50° C., with subsequent removal of byproducts.

It is advisable to remove as much acid as possible before neutralization, in order to reduce the amount of byproducts that must be filtered from the final product. In an embodiment, the amount of acid in the reaction product is reduced by distillation and/or steam stripping to an acid value of less than 15 mgKOH/g, preferably less than about 10 mgKOH/g prior to neutralization. In an embodiment, the final composition is considered to be neutral when the acid value is less than 1.0 mg KOH/g. In an embodiment, the final composition has an acid value is less than 0.5 mg KOH/g, or less than 0.1 mg KOH/g, for example the final acid value is less than 0.05 mg KOH/g.

The present method is carried out by reacting polyol suitable as a component to make useful polyol esters. In an embodiment, the polyol is selected from compounds comprising two hydroxy functionalities. In an embodiment, the polyol is selected from compounds comprising three hydroxy functionalities. In an embodiment, the polyol is selected from compounds comprising four hydroxy functionalities. In an embodiment, the polyol is selected from compounds comprising from five to eight hydroxy functionalities. In an embodiment, the polyol is selected from the group consisting of 1,3-propanediol; 1,3-butanediol; 1,4-butanediol; 1,2-hexanediol; 1,6-hexanediol; neopentyl glycol; trimethylolpropane; penta-erythritol; 2,2,4-trimethylpentane-1,3-diol; glycerol; 3(4), 8(9)-dihydroxymethyltricyclo[5.2.1.0$^{2,6}$]decane; polyglycerol, isosorbide and dipentaerythritol. In an embodiment, the polyol is neopentyl glycol. In an embodiment, the polyol is pentaerythritol. In an embodiment, the polyol is a mixture of two or more different polyols. In an embodiment, at least about 95%, or at least about 99% of the polyol by weight is a single polyol.

Likewise, the present method is carried out by reacting linear or branched aliphatic monocarboxylic C3-20 acid suitable as a component to make useful polyol esters. In an embodiment, the monocarboxylic C3-20 acid is branched at the 2-position of the acid. In an embodiment, the branching at the 2-position of the acid is a C2-C4 alkyl moiety. In an embodiment, the monocarboxylic acid is a C4-16 acid that is branched at the 2-position of the acid with a C2-C4 alkyl moiety. In an embodiment, the monocarboxylic acid is 2-Ethylhexanoic Acid. In an embodiment, the monocarboxylic acid is a mixture of two or more different monocarboxylic acids. In an embodiment, at least about 95%, or at least about 99% of the monocarboxylic acid by weight is a single monocarboxylic acid.

In an embodiment, the high purity polyol esters selected from neopentyl glycol di(2-ethylhexanoate) and pentaerythritol tetra(2-ethylhexanoate) esters As noted above, step b) comprises adding an anhydride of the corresponding linear or branched aliphatic monocarboxylic C3-20 acid to the intermediate reaction composition in an amount of from 1 to about 2.5 equivalents of available OH in the intermediate composition to form a reaction mixture. In an embodiment, the anhydride of the corresponding linear or branched aliphatic monocarboxylic C3-20 acid is added to the intermediate reaction composition in an amount of from 1 to about 1.3 equivalents of available OH in the intermediate composition to form a reaction mixture.

The amount of Grams 2-EH anhydride to add in this step is determined as follows:

[(OH Value)×(270)×(no. equivalents (in range 1.0–2.5))×(*rxn* weight)]/(1000)×(56.1)

In an embodiment, the polyol esters prepared by the present invention have a final hydroxy value maximum of 4.

In an embodiment, the polyol esters prepared by the present invention have a final Total acid number maximum of 0.02.

In an embodiment, the polyol esters prepared by the present invention have a final Water content maximum of 25 ppm. In an embodiment of the present process, water is removed from the product composition containing the polyol ester so prepared, for example, by degassing.

In an embodiment, the polyol esters prepared by the present invention have a final content of any of Al, Ag, Ba, Ca, Cr, Cu, Fe, Mg, Mo, Na, Ni, P, Pb, Si, Sn, Ti, V, Zn that is less than 1 ppm.

In an embodiment, no catalyst comprising metal, halogen or sulfur or bleaching agent comprising metal, halogen or sulfur is present in any of the above method steps a-c as discussed above.

The absence or very low content of catalyst comprising metal, halogen or sulfur or bleaching agent comprising metal, halogen or sulfur in the final product is beneficial because the presence of such materials promotes decompositions of the polyol esters or materials with which the polyol esters are mixed, thereby shortening the useful life of the product and potentially leading to equipment failure.

The use of each of the described embodiments of the high purity polyol esters prepared as described above as a lubricant base for refrigeration equipment, such as compressors, is specifically contemplated as an embodiment of the present invention.

The Hydroxy Value is defined as the number of milligrams of potassium hydroxide equivalent to the hydroxyl content of one gram of sample, and is determined according to AOCS Official Method Cd 13-60.

The acid values determined during the esterification process are measured according to AOCS Official Method CTe 1a-64. This method uses 0.5N potassium hydroxide. The acid values determined during any distillation process are measured according to AOCS Official Method Cd 3-25. This method uses 0.1N potassium hydroxide.

Viscosity is determined according to ASTM D 445 using the Cannon Ubbelohde tubes identified in Table 1 of this ASTM.

EXAMPLES

Representative embodiments of the present invention will now be described with reference to the following examples that illustrate the principles and practice of the present invention.

Preparative Example 1

Preparation of 2-Ethylhexanoic Anhydride

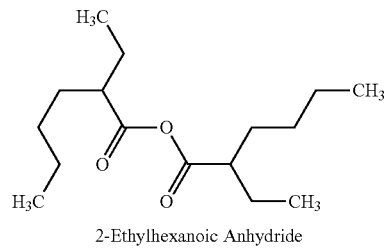 [SMILES: CCCCC(CC)C(=O)OC(=O)C(CC)CCCC]

2-Ethylhexanoic Anhydride

2-Ethylhexanoic Anhydride was prepared by the reaction of 2-ethylhexanoic acid with acetic anhydride under vacuum distillation conditions to remove the acetic acid anhydride co-product. Thus 1.0 mole of acetic anhydride was mixed with 2.05 mole 2-ethylhexanoic and then heated from 140-160° C. under vacuum through a fractionation column of 2-3 plates allowing the acetic acid to condense in a receiver. This acetic acid by-product is of suitable quality to be used in other acetate related products. The high boiling 2-ethylhexanoic anhydride is used as is as an accelerant as described in the invention above.

Comparative Example 1—Standard Process Esterification Rate of 97% in 24 Hours A neopentyl glycol di(2-ethylhexanoate) having an ester content greater than 97% was prepared by reacting during 24 hours at 170-250° C. neopentyl glycol with a 45-50 mol. % excess of 2-ethylhexanoic acid in the presence of 0.1-0.3 weight % activated carbon followed by de-acidification, steam treatment, filtration and subsequent drying. The product color was 46 APHA, hydroxyl number 2.2, acid number 0.12 mg KOH/g and viscosity 6.7 cSt at 40° C. The graph of FIG. 1 clearly shows that the reaction time verses reaction temperature to achieve a residual hydroxyl value suitable for lubricant and plasticizer applications is approximately 24 hours for this step alone. In addition to loss of productivity, color and by-product formation continue throughout this high temperature (220-250° C.) esterification step.

Example 2—Anhydride Accelerated Process Esterification Rate of 97% in 8 Hours Neopentyl glycol di(2-ethylhexanoate) having an ester content greater than 97% was prepared by reacting during 6 hours at 170-250° C. neopentyl glycol with a 45-50 mol. % excess of 2-ethylhexanoic acid in the presence of 0.1-0.3 weight % activated carbon followed by cooling to 150-170° C., adding 10 weight percent 2-ethylhexanoic anhydride and holding at that temperature for 30 minutes. This step was then followed immediately by de-acidification by vacuum distillation through a 5 plate fractionation column, base treatment to remove low levels of 2-ethylhexanoic acid, steam treatment to remove low molecular weight odiferous components, filtration and subsequent vacuum drying. The reaction time verses reaction temperature to achieve a residual hydroxyl value suitable for lubricant and plasticizer applications is approximately 7-8 hours for this step alone. See FIG. 1. In addition to the substantial gain in productivity, color and by-product formation is minimized throughout this high temperature (220-250° C.) shortened esterification step. No presence residual unreacted 2-ethylhexanoic acid anhydride was noted by titration. The product color was 101 APHA, hydroxyl number <1.0, acid number 0.09, and the viscosity was 6.7 cSt at 40° C.

Figure 2:
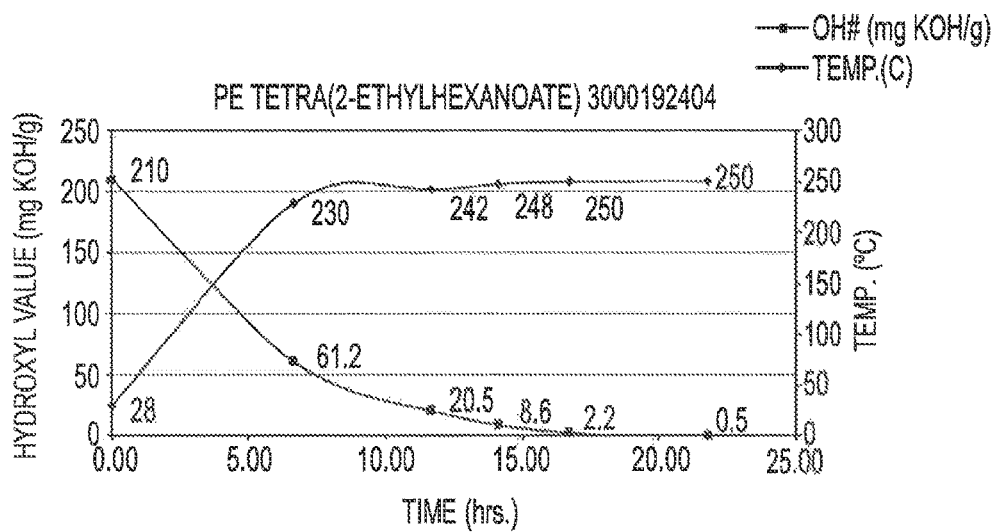
FIG. 2 is a graph showing the reaction time vs reaction temperature of an embodiment of the present method of preparation. "PE" refers to pentaerythritol.

Comparative Example 3—Standard Process Esterification Rate of 97% in 17 Hours A pentaerythritol tetra(2-ethylhexanoate) having an ester content greater than 97% was prepared by reacting during 16-17 hours at 170-250° C. pentaerythritol with a 45-50 mol. % excess of 2-ethylhexanoic acid in the presence of 0.1-0.3 weight % activated carbon followed by de-acidification, steam treatment, filtration and subsequent drying. The product color was 38 APHA, hydroxyl number <3.0 mg KOH/g, acid number 0.02 mg KOH/g and the viscosity 42 cSt @ 40° C. FIG. 2 clearly shows the reaction time vs. reaction temperature to achieve a residual hydroxyl value suitable for lubricant and plasticizer applications is approximately 17 hours for this step alone. In addition to loss of productivity, color and by-product formation continue throughout this high temperature (220-250° C.) esterification step.

Example 4—Anhydride Accelerated Process Esterification Rate of 97% in 6 Hours Pentaerythritol tetra(2-ethylhexanoate) having an ester content greater than 97% was prepared by reacting during 6 hours at 170-250° C. pentaerythritol with a 45-50 mol. % excess of 2-ethylhexanoic acid in the presence of 0.1-0.3 weight % activated carbon followed by cooling the material to 150-170° C., adding 28 weight percent 2-ethylhexanoic anhydride and holding at that temperature for 30 minutes. This step was then followed immediately by de-acidification by vacuum distillation, base treatment to remove low levels of 2-ethylhexanoic acid, steam treatment, filtration and subsequent vacuum drying. The reaction time versus reaction temperature to achieve a residual hydroxyl value suitable for lubricant and plasticizer applications is approximately 5-6 hours for this step alone. See FIG. 2. In addition to the substantial gain in productivity, color and by-product formation is minimized throughout this high temperature (220-250° C.) shortened esterification step. No presence of residual unreacted 2-ethylhexanoic acid anhydride was noted by titration. The product color was 80 APHA, hydroxyl number <2.0 mg KOH/g, acid number 0.01 mg KOH/g, and viscosity 43 cSt at 40 C.

Preparative Example 2

Preparation of 2-Propylheptanoic Anhydride

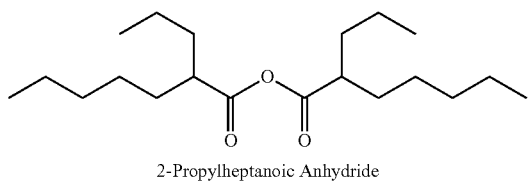 [SMILES: CCCCCC(CCC)C(=O)OC(=O)C(CCC)CCCCC]

2-Propylheptanoic Anhydride

2-Propylheptanoic Anhydride is prepared by the reaction of 2-Propylheptanoic acid with acetic anhydride using reaction conditions and methods as set forth above in Preparative Example 1.

Comparative Example 5—Standard Process Esterification Rate of 97% in 24 Hours A neopentyl glycol di(2-propylheptanoate) having an ester content greater than 97% is prepared by reacting during 24 hours at 170-270° C. neopentyl glycol with a 45-50 mol. % excess of 2-propylheptanoic acid in the presence of 0.1-0.3 weight % activated carbon followed by de-acidification, steam treatment, filtration and subsequent drying. The product color is <50 APHA, hydroxyl number 2.0, acid number <0.10 mg KOH/g and viscosity <10 cSt at 40° C. The reaction time verses reaction temperature to achieve a residual hydroxyl value suitable for lubricant and plasticizer applications is approximately 24 hours for this step alone. In addition to loss of productivity, color and by-product formation continue throughout this high temperature (220-270° C.) esterification step.

Example 5—Anhydride Accelerated Process Esterification Rate of 97% in 8 Hours Neopentyl glycol di(2-propylheptanoate) having an ester content greater than 97% is prepared by reacting during 6 hours at 170-270° C. neopentyl glycol with a 45-50 mol. % excess of 2-propylheptanoic acid in the presence of 0.1-0.3 weight % activated carbon followed by cooling to 150-170° C., adding 10 weight percent 2-propylheptanoic anhydride and holding at that temperature for 30 minutes. This step is then followed immediately by de-acidification by vacuum distillation through a 5 plate fractionation column, base treatment to remove low levels of 2-propylheptanoic acid, steam treatment to remove low molecular weight odiferous components, filtration and subsequent vacuum drying. The reaction time verses reaction temperature to achieve a residual hydroxyl value suitable for lubricant and plasticizer applications is approximately 7-8 hours for this step alone. In addition to the substantial gain in productivity, color and by-product formation is minimized throughout this high temperature (220-250° C.) shortened esterification step. No presence residual unreacted 2-propylheptanoic acid anhydride is noted by titration. The product color is <100 APHA, hydroxyl number <1.0, acid number <0.1, and the viscosity is <10 cSt at 40° C.

Comparative Example 6—Standard Process Esterification Rate of 97% in 17 Hours

A pentaerythritol tetra(2-propylheptanoate) having an ester content greater than 97% is prepared by reacting during 16-17 hours at 170-280° C. pentaerythritol with a 45-50 mol. % excess of 2-propylheptanoic acid in the presence of 0.1-0.3 weight % activated carbon followed by de-acidification, steam treatment, filtration and subsequent drying. The product color is <50 APHA, hydroxyl number <3.0 mg KOH/g, acid number <0.05 mg KOH/g and the viscosity <75 cSt @ 40° C. The reaction time vs. reaction temperature to achieve a residual hydroxyl value suitable for lubricant and plasticizer applications is approximately 15-20 hours for this step alone. In addition to loss of productivity, color and by-product formation continue throughout this high temperature (220-280° C.) esterification step.

Example 6—Anhydride Accelerated Process Esterification Rate of 97% in 6 Hours

Pentaerythritol tetra(2-propylheptanoate) having an ester content greater than 97% is prepared by reacting during 6 hours at 170-270° C. pentaerythritol with a 45-50 mol. % excess of 2-propylheptanoic acid in the presence of 0.1-0.3 weight % activated carbon followed by cooling the material to 150-170° C., adding 28 weight percent 2-propylheptanoic anhydride and holding at that temperature for 30 minutes. This step is then followed immediately by de-acidification by vacuum distillation, base treatment to remove low levels of 2-propylheptanoic acid, steam treatment, filtration and subsequent vacuum drying. The reaction time versus reaction temperature to achieve a residual hydroxyl value suitable for lubricant and plasticizer applications is approximately 5-6 hours for this step alone. In addition to the substantial gain in productivity, color and by-product formation is minimized throughout this high temperature (220-270° C.) shortened esterification step. No presence of residual unreacted 2-propylheptanoic acid anhydride is noted by titration. The product color is <100 APHA, hydroxyl number <<2.0 mg KOH/g, acid number ~0.01 mg KOH/g, and viscosity <50 cSt at 40 C.

As can be seen by in the above examples, the process of the present invention produces high purity polyol esters in a significantly shorter reaction time. This surprising ability to prepare the desired product under less harsh conditions results in a final product having decrease color and decreased formation of undesired byproducts. The present method additionally produces the desired product in shorter time periods, utilizing scarce production facilities more efficiently, resulting in higher productivity as compared to prior art processes.

As used herein, the terms "about" or "approximately" mean within an acceptable range for the particular parameter specified as determined by one of ordinary skill in the art, which will depend in part on how the value is measured or determined, e.g., the limitations of the sample preparation and measurement system. Examples of such limitations include preparing the sample in a wet versus a dry environment, different instruments, variations in sample height, and differing requirements in signal-to-noise ratios. For example, "about" can mean greater or lesser than the value or range of values stated by 1/10 of the stated values, but is not intended to limit any value or range of values to only this broader definition. For instance, a concentration value of about 30% means a concentration between 27% and 33%. Each value or range of values preceded by the term "about" is also intended to encompass the embodiment of the stated absolute value or range of values.

Throughout this specification and claims, unless the context requires otherwise, the word "comprise", and variations such as "comprises" and "comprising", will be understood to imply the inclusion of a stated integer or step or group of integers or steps but not the exclusion of any other integer or step or group of integer or step. When used herein "consisting of" excludes any element, step, or ingredient not specified in the claim element. When used herein, "consisting essentially of" does not exclude materials or steps that do not materially affect the basic and novel characteristics of the claim. In the present disclosure of various embodiments, any of the terms "comprising", "consisting essentially of" and "consisting of" used in the description of an embodiment may be replaced with either of the other two terms.

All patents, patent applications (including provisional applications), and publications cited herein are incorporated by reference as if individually incorporated for all purposes. Unless otherwise indicated, all parts and percentages are by weight and all molecular weights are weight average molecular weights. The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of producing high purity polyol esters comprising:
    a) reacting a polyol with an excess amount of a linear or branched aliphatic monocarboxylic C3-20 acid to esterify less than the total amount of the polyol present to form an intermediate reaction composition having a hydroxyl value of from 7 to about 50 mg KOH/g;
    b) adding an anhydride of the corresponding linear or branched aliphatic monocarboxylic C3-20 acid to the intermediate reaction composition in an amount of from 1 to about 2.5 equivalents of available OH in the intermediate composition to form a reaction mixture;
    c) heating the reaction mixture for 5-30 minutes or until all of the corresponding anhydride has reacted to form a reaction product; and
    d) de-acidifying the reaction product;
wherein no catalyst comprising metal, halogen or sulfur or bleaching agent comprising metal, halogen or sulfur is present in any of the above method steps a-c at a concentration above about 15 ppm.

2. The method of claim 1, wherein the intermediate reaction composition has a hydroxyl value of from about 8 to about 40 mg KOH/g.

3. The method of claim 1, wherein the intermediate reaction composition has a hydroxyl value of from about 9 to about 30 mg KOH/g.

4. The method of claim 1, wherein the intermediate reaction composition has a hydroxyl value of from about 10 to about 25 mg KOH/g.

5. The method of claim 1, wherein steps a-c are carried out at ambient pressure.

6. The method of claim 1, wherein step a) is carried out at a temperature of from about 170° C. to about 230° C.

7. The method of claim 1, wherein step a) is carried out for at time of from about 3 to about 5 hours.

8. The method of claim 1, wherein step c) is carried out at a temperature of from about 150° C. to about 170° C.

9. The method of claim 1, wherein steps a-c are carried out in the presence of an adsorbent.

10. The method of claim 9, wherein the adsorbent is activated carbon.

11. The method of claim 1, wherein step d) comprises vacuum distillation and steam treatment to remove acid and water.

12. The method of claim 1, further comprising the steps of filtration and drying.

13. The method of claim 1, wherein the polyol is selected from the group consisting of 1,3-propanediol; 1,3-butanediol; 1,4-butanediol; 1,2-hexanediol; 1,6-hexanediol; neopentyl glycol; trimethylolpropane; penta-erythritol; 2,2,4-trimethylpentane-1,3-diol; glycerol; polyglycerol, isosorbide and 3(4), 8(9)-dihydroxymethyltricyclo[$5.2.1.0^{2,6}$]decane.

14. The method of claim 1, wherein the polyol is neopentyl glycol.

15. The method of claim 1, wherein the monocarboxylic C3-20 acid is branched at the 2-position of the acid.

16. The method of claim 15, wherein the branching at the 2-position of the acid is a C2-C4 alkyl moiety.

17. The method of claim 1, wherein the monocarboxylic acid is a C4-16 acid that is branched at the 2-position of the acid with a C2-C4 alkyl moiety.

18. The method of claim 1, wherein the monocarboxylic acid is 2-Ethylhexanoic Acid.

19. The method of claim 1, wherein the monocarboxylic acid is 2-propylheptanoic acid.

20. The method of claim 1, wherein the final product has a hydroxyl value of less than about 1 mg KOH/g.

* * * * *